US010729379B2

(12) United States Patent
Cheng et al.

(10) Patent No.: US 10,729,379 B2
(45) Date of Patent: Aug. 4, 2020

(54) ELECTRICAL WEARABLE CAPACITIVE BIOSENSOR AND NOISE ARTIFACT SUPPRESSION METHOD

(71) Applicant: The Regents of the University of California, Oakland, CA (US)

(72) Inventors: Chung-Kuan Cheng, San Diego, CA (US); Patrick Mercier, La Jolla, CA (US); Shih-Hung Weng, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 931 days.

(21) Appl. No.: 15/031,142

(22) PCT Filed: Oct. 21, 2014

(86) PCT No.: PCT/US2014/061520
§ 371 (c)(1),
(2) Date: Apr. 21, 2016

(87) PCT Pub. No.: WO2015/061282
PCT Pub. Date: Apr. 30, 2015

(65) Prior Publication Data
US 2016/0256111 A1 Sep. 8, 2016

Related U.S. Application Data

(60) Provisional application No. 61/894,151, filed on Oct. 22, 2013.

(51) Int. Cl.
*A61B 5/00* (2006.01)
*A61B 5/0428* (2006.01)
*A61B 5/0408* (2006.01)

(52) U.S. Cl.
CPC .......... *A61B 5/7203* (2013.01); *A61B 5/0002* (2013.01); *A61B 5/0408* (2013.01);
(Continued)

(58) Field of Classification Search
CPC . A61B 5/0402; A61B 5/0408; A61B 5/04284; A61B 5/7203; A61B 2561/0214; A61B 2561/18; A61B 2561/182
See application file for complete search history.

(56) References Cited

U.S. PATENT DOCUMENTS

| 6,032,072 A | 2/2000 | Greenwald et al. |
| 2004/0073104 A1 | 4/2004 | Brun del Re et al. |

(Continued)

OTHER PUBLICATIONS

E. M. Spinelli, N. H. Martinez and M. A. Mayosky, "A transconductance driven-right-leg circuit," in IEEE Transactions on Biomedical Engineering, vol. 46, No. 12, pp. 1466-1470, Dec. 1999.
(Continued)

*Primary Examiner* — Eun Hwa Kim
*Assistant Examiner* — James A Cipriano
(74) *Attorney, Agent, or Firm* — Greer, Burns & Crain; Steven P. Fallon (57) ABSTRACT

A biosensor of the invention is a capacitive noncontact sensor with two sensor channels split into a plurality of physically interdigitated symmetrical electrodes and shield sections. Two capacitive plates are electrically connected to the two sensor channels. The capacitive noncontact sensor is sized and packaged to be worn by a person to place the capacitive plates close to the skin of the person and form first and second channel input capacitors with the skin. A signal reconstruction circuit obtains a bio signal from the first and second channel input capacitors through the electrodes by reconstructing differences in the two sensor channels. The circuit includes different parasitic input capacitance in the
(Continued)

two channels to create channel-specific outputs that depend on input coupling capacitance.

8 Claims, 8 Drawing Sheets

(52) U.S. Cl.
CPC ........ *A61B 5/04284* (2013.01); *A61B 5/6802* (2013.01); *A61B 5/7225* (2013.01); *A61B 2562/166* (2013.01); *A61B 2562/182* (2013.01)

(56) References Cited

U.S. PATENT DOCUMENTS

| | | | | |
|---|---|---|---|---|
| 2010/0198044 | A1* | 8/2010 | Gehman | A61B 5/0408 600/393 |
| 2011/0137200 | A1* | 6/2011 | Yin | A61B 5/04085 600/547 |
| 2012/0116198 | A1* | 5/2012 | Veen | A61B 5/04284 600/372 |
| 2012/0116201 | A1* | 5/2012 | Zdeblick | A61B 5/681 600/382 |
| 2012/0245436 | A1* | 9/2012 | Rutkove | A61B 5/4519 600/301 |

OTHER PUBLICATIONS

F. Hosseini, D. Schroeder and W. H. Krautschneider, "Capacitive sensors for detection of the movement artifacts in active capacitive electrocardiography electrodes," The 5th 2012 Biomedical Engineering International Conference, Ubon Ratchathani, 2012, pp. 1-4.

A. S. Arani, Y. Zhu, Y. Cheng, C. Cheng, S. Lin and P. Chen, "Exploring Cardioneural Signals from Noninvasive ECG Measurement," 2007 IEEE 7th International Symposium on BioInformatics and BioEngineering, Boston, MA, 2007, pp. 1134-1138.

* cited by examiner

ELECTRICAL WEARABLE CAPACITIVE BIOSENSOR AND NOISE ARTIFACT SUPPRESSION METHOD

PRIORITY CLAIM AND REFERENCE TO RELATED APPLICATION

The application claims priority under 35 U.S.C. § 119 and all applicable treaties from prior provisional application Ser. No. 61/894,151, which was filed Oct. 22, 2013.

STATEMENT OF GOVERNMENT INTEREST

This invention was made with government support under CCF-1017864 awarded by National Science Foundation. The government has certain rights in the invention.

FIELD

A field of the invention is bio-sensing. Example applications of the invention include non-contact bio-potential acquisition systems.

BACKGROUND

Biological conditions are most often monitored in clinical settings. While effective in many situations, clinical tests will often fail to detect rare or transient events. Daily wearable sensors and systems are needed for ambulatory data collection over extended periods of time.

Even clinical testing systems have drawbacks. Biological testing, such as during stress testing, is most often conducted clinically with ECG (electrocardiography) or EEG (electroencephalography) measurements. The ECG systems record heart activity. EEG systems record brain activity. Both systems detect electrical signals from multiple electrodes that are adhered to the skin for data collection. Typical electrodes are wet electrodes, which are employed to attempt to reduce interference from impedance with the skin to electrode interface. However, the wet electrodes cause skin irritation and discomfort when conductive gel or paste is adhered to skin for low-impedance electrical connections. In addition, a large number of electrodes at discrete locations are used to obtain independent signals. The many-wire architecture from body to instrument can take extensive time for preparation, can constraint normal body motion, and electrodes are often loosened during testing and fall off.

This has been a long recognized problem, but the ECG and EEG systems with wet contact electrodes remain state of the art. Prior efforts to improve the ECG and EEG systems have focused on non-contact sensing. An early system introduced capacitive coupling to the skin. See, P. C. Richardson, "The insulated electrode: A pasteless electrocardiographic technique," Proc. Annu. Conf. Eng. Med. Biol. (ACEMB'20), vol 9, p. 157 (1967). Research into the non-contact sensing techniques have continued for decades. See, e.g., Farzad Hosseini, Dietmar Schroeder and Wolfgang H. Krautschneider, "Capacitive sensors for Detection of the Movement Artifacts in Active Capacitive Electrocardiography Electrodes", Biomedical Engineering International Conference (BMEiCON), pp. 1-4 (2012). These non-contact methods don't require a direct connection with skin and allow for electrodes to be in clothing or applied with small adhesive patches. After decades of research in non-contact sensing, the ECG and EEG wet electrodes remain important because the non-contact sensing still suffers from excessive noise due to movement between the subject and sensor and because of triboelectricity. Other sources of noise include environmental interference (caused by active grounding resulting from surface contact) and high frequency noise created by muscles.

SUMMARY OF THE INVENTION

An embodiment of the invention is a method for suppressing noise and recovering a signal of interest from a bio-sensor obtains separate signals from two sensor channels. The two channels are associated with separate sensor electrodes. Capacitor plates obtain biosignals for the two channels, which provide different input load capacitances. Input coupling capacitance is determined for the bio-sensor by using the different input load capacitances. The bio signal is recovered with the calculated input capacitance.

A preferred biosensor of the invention is a capacitive noncontact sensor with two sensor channels split into a plurality of physically interdigitated symmetrical electrodes and shield sections. Two capacitive plates are electrically connected to the two sensor channels. The capacitive non-contact sensor is sized and packaged to be worn by a person to place the capacitive plates close to the skin of the person and form first and second channel input capacitors with the skin. A signal reconstruction circuit obtains a bio signal from the first and second channel input capacitors through the electrodes by reconstructing differences in the two sensor channels. The circuit includes different parasitic input capacitance in the two channels to create channel-specific outputs that depend on input coupling capacitance.

DESCRIPTION OF THE PREFERRED EMBODIMENTS

A preferred embodiment electrical wearable bio-sensor of the invention includes a plurality of physically-interleaved capacitive channels. The separate channels have different amounts of parasitic input capacitance that create channel specific outputs that depend upon input coupling capacitance. Differences in the output channels are processed with a digital reconstruction filter to re-create the original biopotential with attenuated motion artifacts. Preferred embodiments provide non-contact sensors, i.e., sensors that can be carried on clothing or worn on body parts with patches or bands and without requiring direct contact with the skin.

A preferred sensor includes a plurality of interleaved symmetrical channel electrodes. Two channels each include a plurality of shaped electrodes that are electrically isolated from each other but electrically connected to each in a signal layer. A particular preferred embodiment includes a plurality of pie piece shaped electrodes. First channel electrodes and second channel electrodes alternate and are isolated from each other. The first channel electrodes are connected to each other in a signal layer through vias. Second channel electrodes are connected to each other with an outer ring conductor. In a shield layer the second channel shield sections are slightly larger and extend to the outer ring while the first channel shield sections are isolated from the outer ring conductor. The connections create an active shield via feedback such that each of the two channels has its own shield.

In preferred embodiments noise artifacts for a capacitive sensor are attenuated by employing a two-channel biopotential front-end with different transfer functions between channels, permitting a digital signal processor to solve a system of equations that can reconstruct both the noise-induced (such as motion induced) time-varying coupling capacitance, as well as the undistorted biopotential signal.

A preferred embodiment sensor can be applied, for example, to clothing and need not be in intimate contact with a subject being monitored. In preferred embodiment systems of the invention, signals are collected wirelessly, such as by a smart phone or other portable computer. In a preferred embodiment, the sensor is a non-contact sensor having multiple electrodes are insulated and embedded within a subject's clothing close to the heart for monitoring of ECG signals.

Preferred methods use two electrodes with different load capacitances. Two voltage output channels are used to recover the input capacitance that can be attributed to noise, e.g. triboelectricity. The coupling capacitance is used to recover the body signal.

Preferred embodiments provide a wearable sensing system to monitor bio potentials via noncontact capacitive sensors that are suitable for long-term and ambulatory monitoring applications. Motion artifact suppression is provided by sensors and systems of the invention. The sensor provides a pair of physically-interleaved capacitive channels designed to have different amounts of parasitic input capacitance, which create a channel-specific outputs that depend on the input coupling capacitance itself. Differences in output channel results can then be reconstructed with a digital filter to re-create the original bio potential with attenuated motion artifacts.

Preferably, all capacitive sections in a bio-sensor of the invention are located on a bottom layer of a PCB. A separate electrode operates as driven-right-leg circuit to provide common-mode noise suppression. Amplified output signals from each channel are digitized by an ADC, and in preferred embodiments an on-board Bluetooth module is used to deliver sensed information to a computer device, such as a portable computer, a PC, a tablet, a smart phone or the like. A shielded cable is used to connect two PCBs for external noise cancellation.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

Figure 1A:
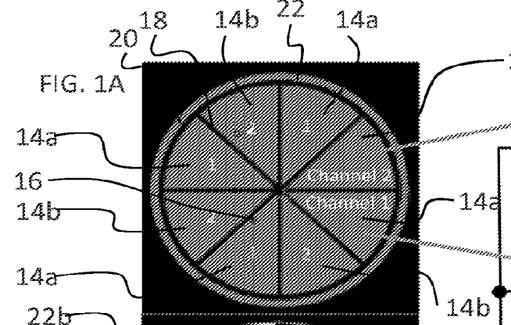
FIGS. 1A and 1B respectively show the electrode layer and shield layer of a preferred embodiment interdigitated PCB capacitor biosensor of the invention and FIG. 1C shows the front end of a sensing circuit of the invention.
Figure 1B:
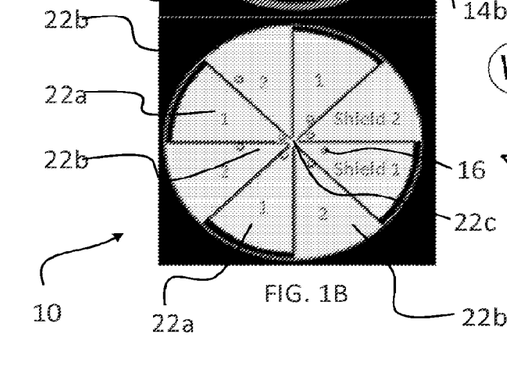
Figure 1C:
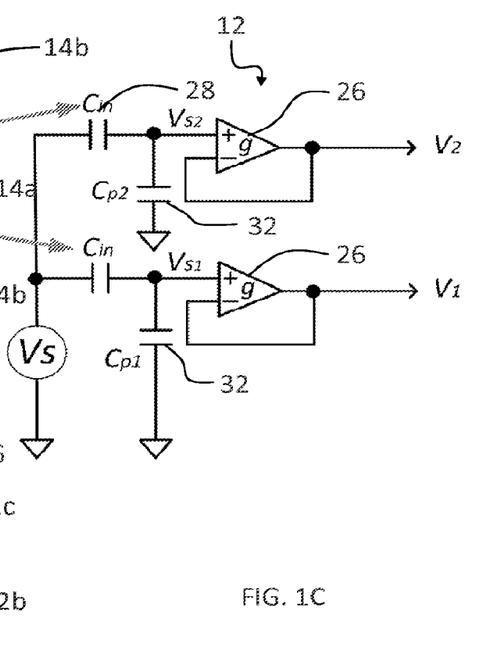

FIGS. 1A-1C illustrate a preferred embodiment bio sensor 10 of the invention and a front end of a sensing circuit 12. FIG. 1A shows an electrode layer and FIG. 1B shows a shield layer. The sensor includes at least two independent electrodes 14a and 14b in a symmetrical arrangement, that each are formed from a plurality of same-shaped symmetric pie piece shaped sections of conductors. As seen in FIGS. 1A and 1B, the pie piece shape is generally triangular with an apex opposite an arcuate end. The pie piece shape is preferred to form a circular biosensor, but other symmetrical shapes can also be used. The first and second electrodes should be substantially equal in area and symmetrical in shape. The goal is to create an active shield for each channel. The first electrode sections 14a are connected to each other with vias 16 in a signal layer. In preferred embodiments, a PCB 17 (FIG. 2) provides the layers and isolation of the electrodes 14a, 14b. In particular preferred embodiments the two isolated electrodes are both part of a single PCB 17, that provides the support for the biosensor and the various layers. In the preferred embodiment of FIGS. 1A and 1B, channels are split into four interdigitated capacitive sections 14a and 14b. Dielectric 18 isolates the electrode sections 14a and 14b from each other and from an outer conductor ring 20. The conductor ring 20 extends to the shield layer shown in FIG. 1B, where it is isolated from channel 1 shield sections 22a but interconnects channel 2 shield sections 22b. The shield sections 22a are slightly smaller and connect to each other in the middle portion 22c. All of the shield portions 22a and 22b are connected to the signal layer with vias 16. Some of the via through holes 16 connect electrodes to the capacitors Cp1 and Cp2 in a signal layer.

Figure 2:
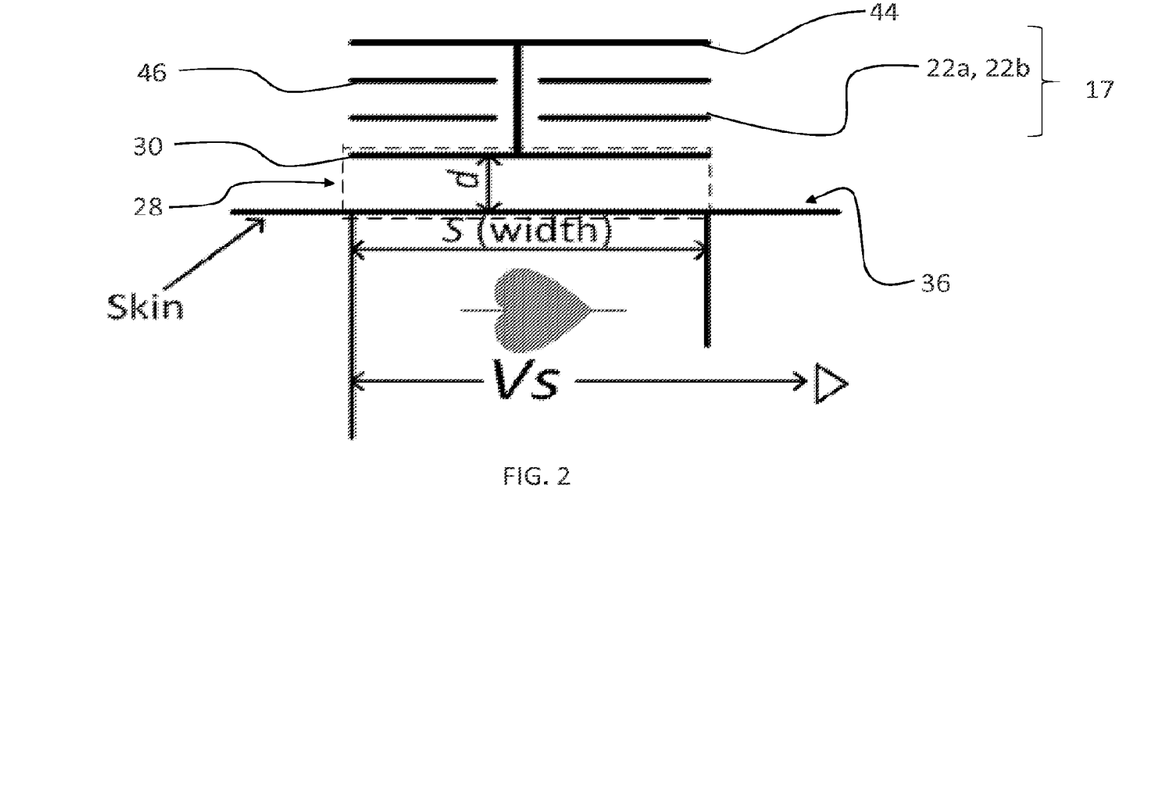
FIG. 2 is a schematic diagram of a cross-section of the PCB capacitor sensor of FIG. 1A.
Figure 3:
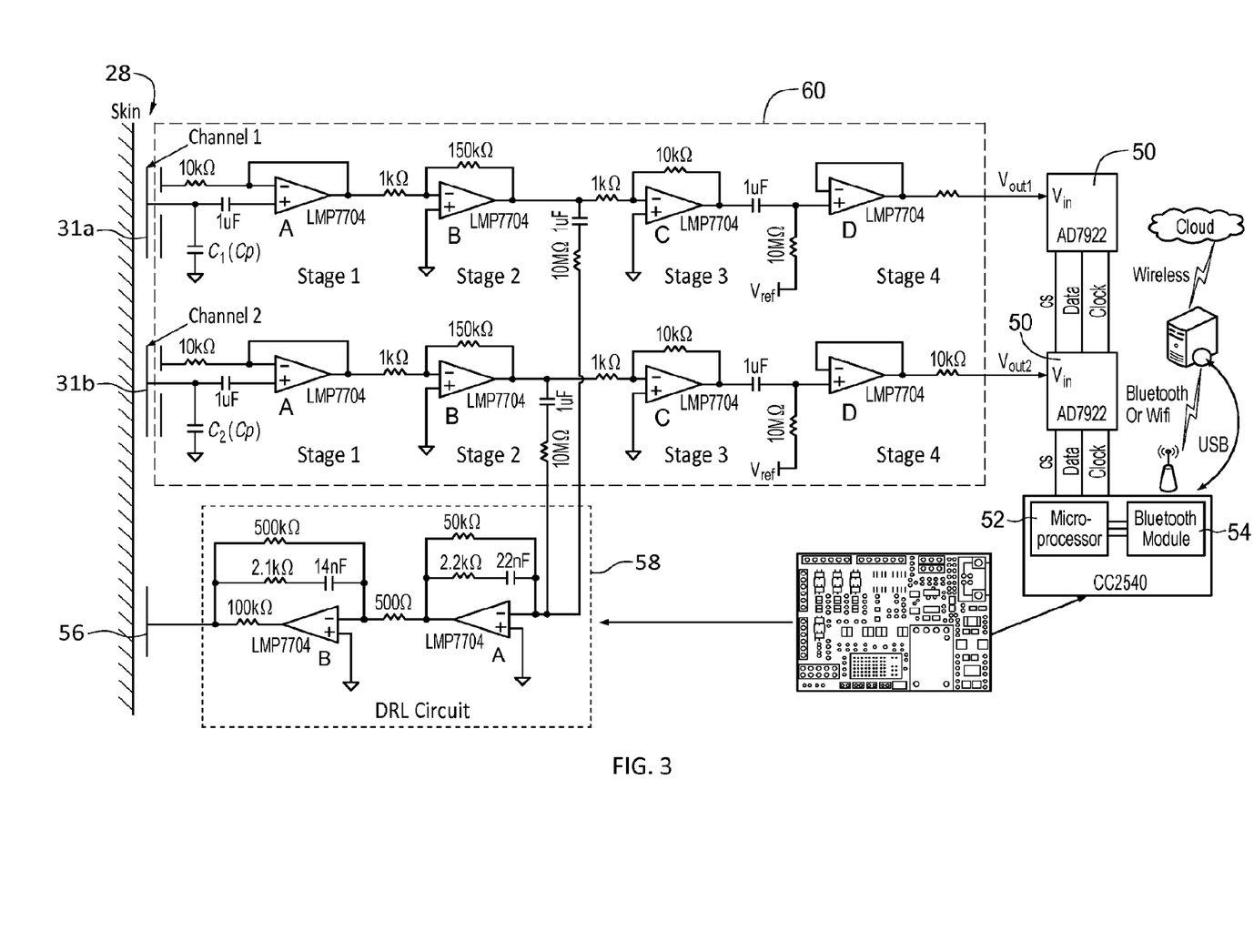
FIG. 3 illustrates a preferred embodiment experimental system of the invention that was constructed to test the invention.

FIG. 1C is a simplified illustration of the first stage 12 of a preferred embodiment amplification circuit in a system of the invention. The biosignal, modeled as $V_s$, is coupled to the input of an amplifier 26 via an input capacitor $C_{in}$ 28, which is realized between the biosensor and the skin of a user of the biosensor. As seen in FIG. 2, a bottom PCB layer 30 (which is conductive) acts as one of the plates of this capacitor $C_{in}$, (the body represents the other plate). The bottom layer 30 includes two capacitor plates, one for each of the two channels. The plates 31a and 31b are shown in FIG. 3. The load capacitance, $C_{p\{1,2\}}$, is composed of the parasitic input capacitance of the amplifier 26 in parallel with a small amount of capacitance that is added with a small capacitor 32. The added capacitance is distinctly different between the two channels, which facilitates signal reconstruction during variations of $C_{in}$.

FIG. 2 illustrates the bio-sensor, which forms the input capacitor $C_{in}$ 28 between the bottom layer 30 and its plates 31a and 31b and the skin 36 of a user. The actual value of $C_{in}$ is given by $$C_{in} = \varepsilon_0 \varepsilon_r \frac{A}{d}, \quad \text{(Eq. 1)}$$

where A is the area of two plates 31a or 31b (FIG. 3), skin that overlap. Distance d is the separation between the two plates 31a or 31b, skin 36. $\varepsilon_0$ is the electric constant. $\varepsilon_r$ is the relative dielectric constant of insulating material, such as solder mask, and air trapped between plates. The dielectric constant can be influenced also by environmental conditions, e.g. sweat, hair and clothing that can be caught between the two capacitor plates.

The physical construction of a particular preferred embodiment of the FIG. 2 sensor includes consists of copper pours on the bottom layer 30 of the PCB that form the plates 31a or 31b. The plates and the sensor as a whole are covered with a protective layer of dielectric or insulating materials such as a polymer or, as in the experimental embodiment, a solder mask. A shield layer consists of the shields for channel 1 and channel 2 22a and 22b, and acts as an active shield that isolates the capacitor 28 from interference of a signal layer 44. A ground plane 46 provides ground to circuits of the signal layer. In order to ensure that $C_{in}$, remains constant in each channel, regardless of electrode tilt or rotation, the channel capacitors are each split into four physically interleaved slices; all slices of each channel are connected together in upper PCB layers Since A, $\epsilon_0$, and $\epsilon_r$ are constants in Eqn. 1, $C_{in}$ will vary with d, which in turn varies with time during motion caused by movement of a user or other events that can cause relative movement between the bio sensor 10 and the user. Equation 2 describes the transfer function of a single-channel, illustrating how a change in $C_{in}$ can introduce distortions in the output $$V_{out} = \text{Gain} \times \frac{V_s(t) \times C_{in}(t) + Q(t)}{C_{in}(t) + C_p}, \quad \text{(Eq. 2)}$$

where Q(t) describes the charge at amplifier input node. This is assumed constant for simplicity of explanation, but triboelectricity can affect Q(t).

Methods, sensors and circuits of the invention provide for suppression of noise from a bio sensor having a plurality of channels. With two distinct load capacitances, the two outputs are first used to recover the input coupling capacitance. The coupling capacitance is then used to recover the signal of interest. The channels are assumed to have the same input coupling capacitance. Preferred sensor constructions as in FIGS. 1A-2 reduce the potential for variation in the input capacitance of the two channels with common construction and location.

In addition, a preferred a noise removal technique can suppress the impact of $C_{in}$ variation through hardware-algorithmic co-design. Q is the charge on the input nodes $V_1$ and $V_2$. Q can be estimated and set for standard circumstances, and software can test from a range of values determined experimentally. This makes Q a constant for the purpose of determining the $C_{in}$ variation. Assuming that Q from electrostatic charge is constant, $V_1$ and $V_2$ can be obtained from a pair of channels while setting $C_p$ as different values: $C_{p1}$ and $C_{p2}$. $C_{p1}$ and $C_{p2}$ should be as small as possible, while also have a difference between. Example values are 5 pico farad and 10 pico farad. The lower bound is the intrinsic capacitor of the op amp in stage 1. The upper bound is the bio sensor signal. The capacitance of $C_{p1}$ and $C_{p2}$ can't reduce the signal too much. The output of each channel is then $$V_1 = \text{Gain} \times \frac{V_s(t) \times C_{in}(t) + Q_1}{C_{in}(t) + C_{p1}} \quad \& \quad \text{(Eq. 3)}$$

$$V_2 = \text{Gain} \times \frac{V_s(t) \times C_{in}(t) + Q_2}{C_{in}(t) + C_{p2}}. \quad \text{(Eq. 4)}$$

Using equations 3 and 4, the input coupling capacitance can be determined as follows:

$$C_{in}(t) = \frac{(Q_2 - Q_1) + (C_{p1} \times V_1 - C_{p2} \times V_2)}{V_2 - V_1} \quad \text{Eq 6}$$

With equations 2 and 6, the signal of interest can then be recovered as follows:

$$V_s(t) = \frac{1}{\text{Gain}} \times \frac{V_1 \times C_{in}(t) + (C_{p1} - Q_1)}{C_{in}(t)} \quad \text{Eq 7}$$

This provides a signal of the biopotential that removes motion artifacts. FIG. 3 illustrates a bio sensor system of the invention, including additional stages of the amplification circuit of the bio sensor and its wireless interface. Stage 1 for channels 1 and 2 is the front end circuit 12 of FIG. 1C as stage 1. The additional stages of front end amplifier circuit are shown, and the amplified circuit is for a biosensor as shown in FIG. 1A-2 including two channels. Since the input coupling capacitances in non-contact sensing applications are small (1-10 pF), the output impedance is preferably in excess of 1 TΩ. The first stage of amplification in the FIG. 3 embodiment is configured as a unity-gain voltage buffer to increase impedance. To ensure sufficiently high input impedance, no external biasing resistor is required, as the internal leakage of the op-amps set the DC operating point. A 10 kΩ resistor and 1 uF capacitor are used to protect and isolate the input of the amplifier from the active shield.

Figure 4:
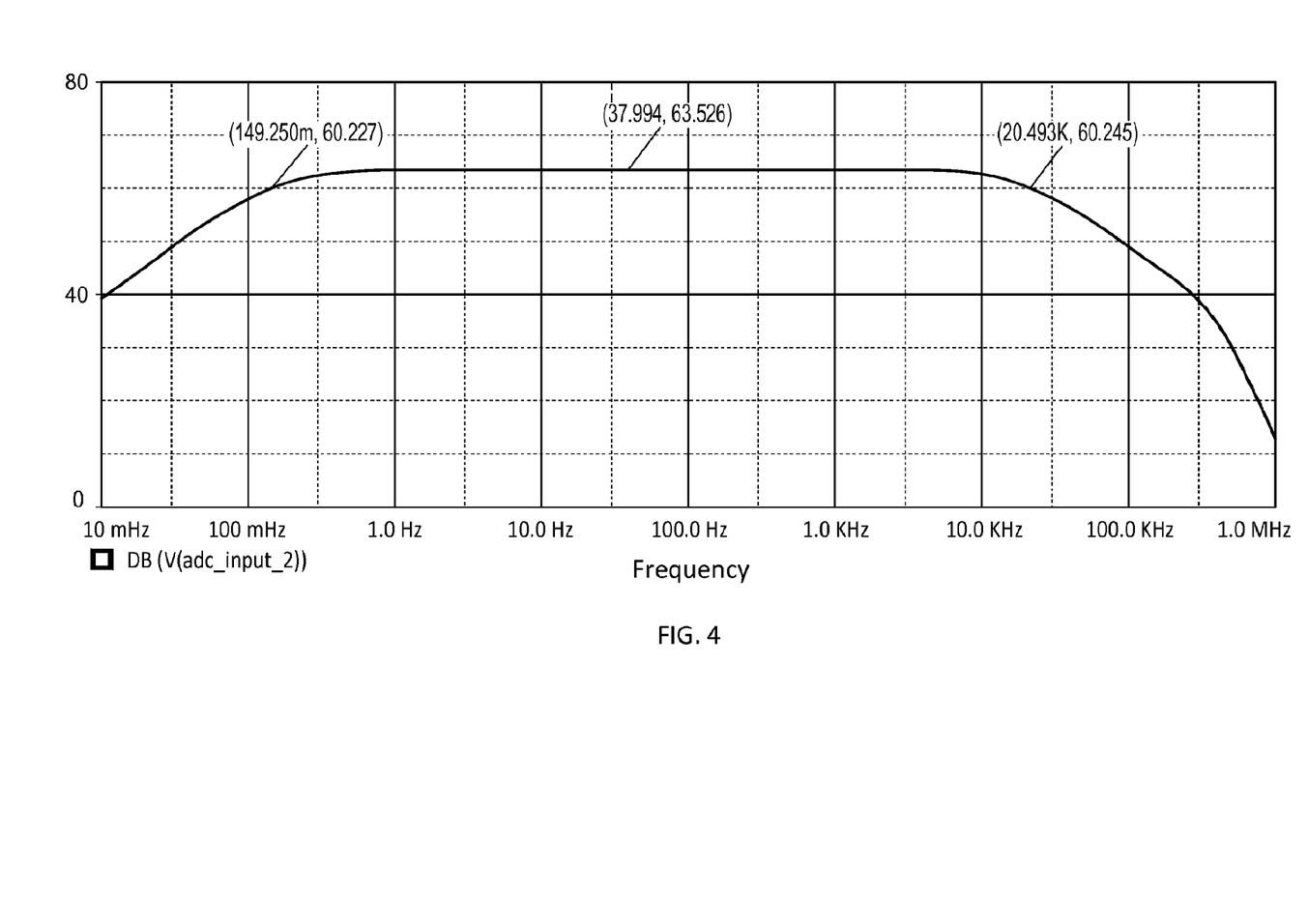
FIG. 4 illustrates the frequency response curve of the multi-stage amplifier in the experimental system.

The first stage unity gain buffer introduces gain loss, due to the parasitic input capacitance. The second and third stages of amplification provide gain (a combined 63.5 dB of gain in an experimental embodiment, as shown in the single channel frequency response plot of FIG. 4). The example preferred two-stage amplifier obtains better gain-bandwidth, 63.5 dB gain with 3 dB frequency 0.1 Hz-20 kHz compared to one-stage amplification. The fourth and final stage biases the signal to 1.35V, which is the common mode voltage for an ADC 50, preferably a separate ADC for each channel, which can run upwards of 1 MSPS. A further low-pass filter is then added in software in the microprocessor 52 that is part of a chip that also includes a Bluetooth or other wireless interface 54.

The body is floated due to the capacitive electrodes, and a floating body is very sensitive to external common-mode noise. A capacitive coupled drive back to the body addresses this issue. Specifically, a dummy electrode 56 with a DRL (Driven-Right-Leg) circuit 58 is used as capacitive ground electrode. In preferred embodiments, the circuit 58 and electronic components outside are a separate component from a biosensor component package 60. The biosensor package 60 includes the biosensor of FIGS. 1A-2 in a protective dielectric coating, such as a polymer. Other components can be worn separately away from the sensor. The DRL circuit 58 and other electronics can be packaged separately. The Bluetooth module can communicate with a handheld device, such as smartphone, or with a computer. Data can be communicated via cloud computing to sports analysis programs, websites, to medical records, to health analysis sites, etc. Actively driven grounding schemes are a known technique to reduce common-mode interference and have been successfully adapted for capacitive sensors. See, Enrique Mario Spinelli, et al., "A Transconductance Driven-Right-Leg Circuit", IEEE Transaction on Biomedical Engineering, Vol. 46, No. 12, pp. 1466-1470, December (1999); Ko Keun Kim, Yong Kyu Lim, and Kwang Suk Park, "Common Mode Noise Cancellation for Electrically Non-Contact ECG Measurement System on a Chair", Proc. 27th Annu Int. Conf. Engineering Medicine Biol. Soc. IEEE-EMBS, pp. 5881-5883 (2005). In the FIG. 3 embodiment, common-mode feedback consists of Input buffer stage 1, amplification stage 2, and the DRL circuit. Without the common mode feedback loop the common mode voltage can easily be amplified and saturate the circuits.

Experimental Data

The FIG. 3 embodiment was constructed and tested. Details of the construction are provided for illustration of a preferred embodiment, but the details do not limit the invention in its broader aspects. Experimental data demonstrates effectiveness of bio-sensors and systems of the invention.

In the experiment, LMP7704, a CMOS quad amplifier in a dual SOIC-14 package with an input structure suitable for ultra-high impedance sensors were used as the operational amplifiers. The devices have an extremely low input bias current of 200 fA (typical) and an input-referred voltage noise of 9 nV/$\sqrt{\text{Hz}}$ (typical). In addition, the LMP7704 is specified to operate at a much lower supply voltage (down to 2.7V) and supply current 2.9 mA.

In the experiments, the sensor consistent with FIGS. 1A, 1B and 2 was manufactured on a standard PCB with an FR-4 substrate. A second PCB board contains the ADCs, Bluetooth module, and power supply. A shielded 6-wire cable is used in the experiments to provide signal transmission, power, and ground between the two boards. During routing of the signal traces, the input pins of the OP-Amps were carefully shielded to prevent crosstalk noise from other parts in circuits. Separating the power supplies reduce the digital noise impact to analog circuits.

The experimental system was powered from a 900 mAh rechargeable lithium-polymer battery that is sufficient for approximately 20 hours of continuous recording, as the LMP7704 requires 2.9 mA, the AD7922 1.6 mA, and the PAN1720 15 mA.

Performance simulations were conducted on the experimental system. A Holter record served as the simulated biosignal. See, A. Shayan-Arani, Y. Zhu, Y. N. Cheng, C. K. Cheng, S. F. Lin, and P. S. Chen, "Exploring Cardioneural Signals from Noninvasive ECG Measurement," IEEE Symp. on Bioinformatics & Bioengineering, pp. 1134-1138 (2007). The noise was modeled with 0.2 µA, 60 Hz common-mode current in parallel with a 300 pF capacitor as the capacitance of the body.

Figure 5A:
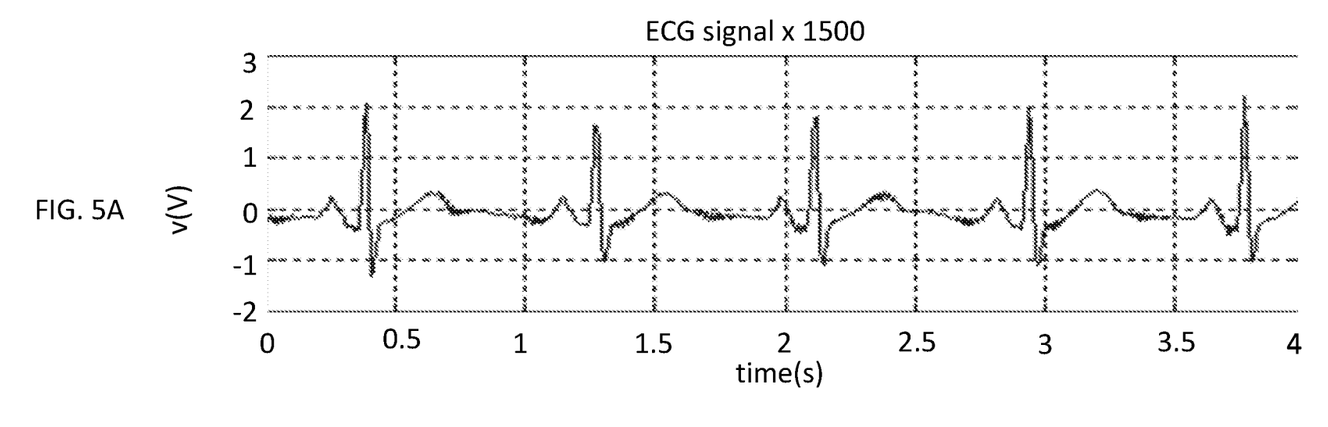
FIGS. 5A and 5B respectively illustrate an input signal and capacitive signal applied to simulate operation of the experimental system.
Figure 5B:
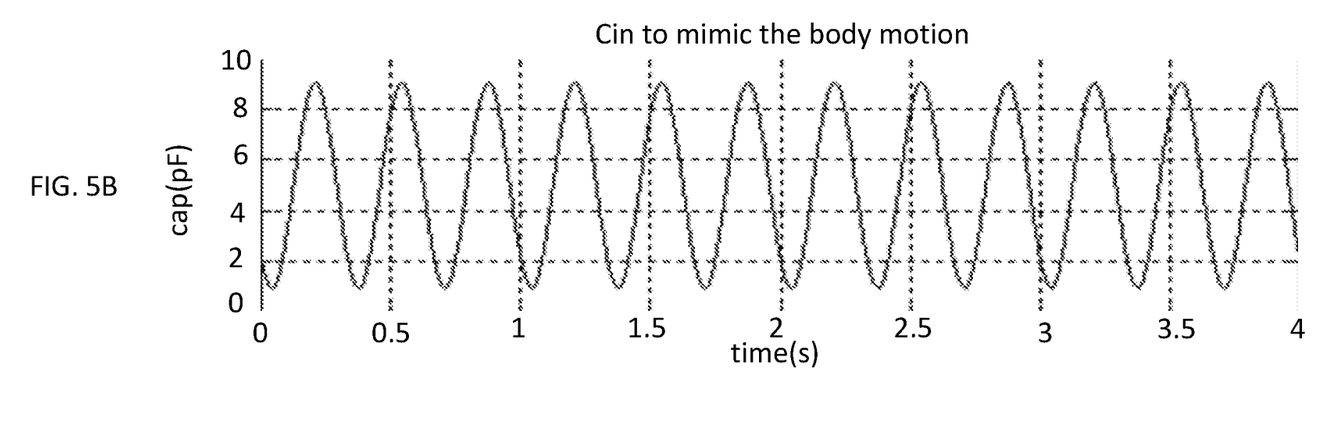

FIGS. 5A and 5B respectively illustrate the original input signal, Vs, and the time-varying capacitance, $C_{in}$, used to emulate motion-induced fluctuations. In the simulation, a sinusoidal capacitance variance with mean of 5 pF, amplitude of 4 pF, and frequency of 3 Hz was employed.

Figure 6A:
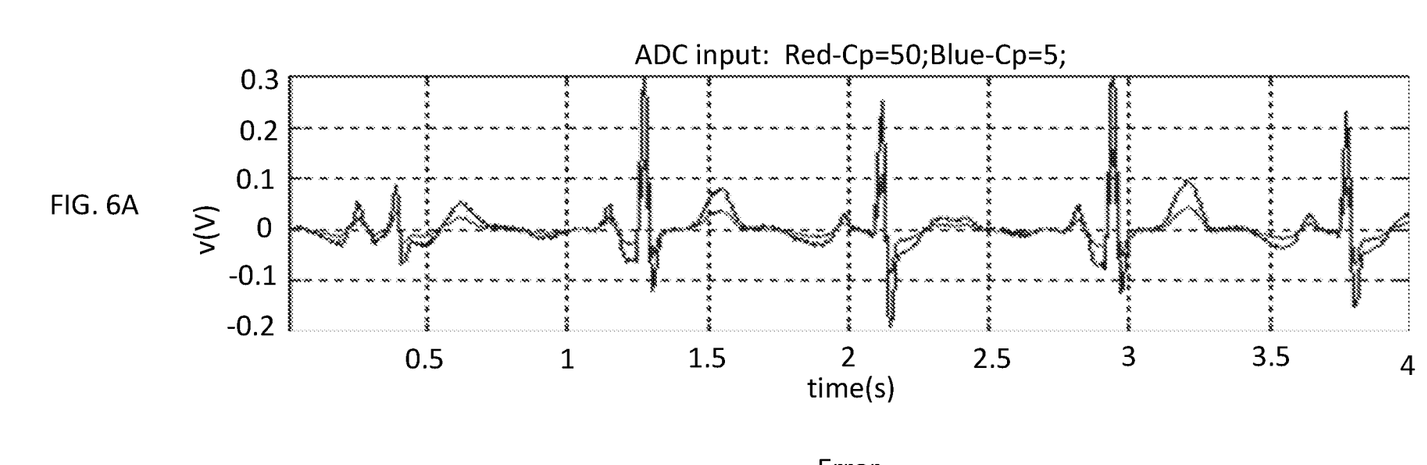
FIG. 6A illustrate outputs of the two channels of a single biosensor.
Figure 6B:
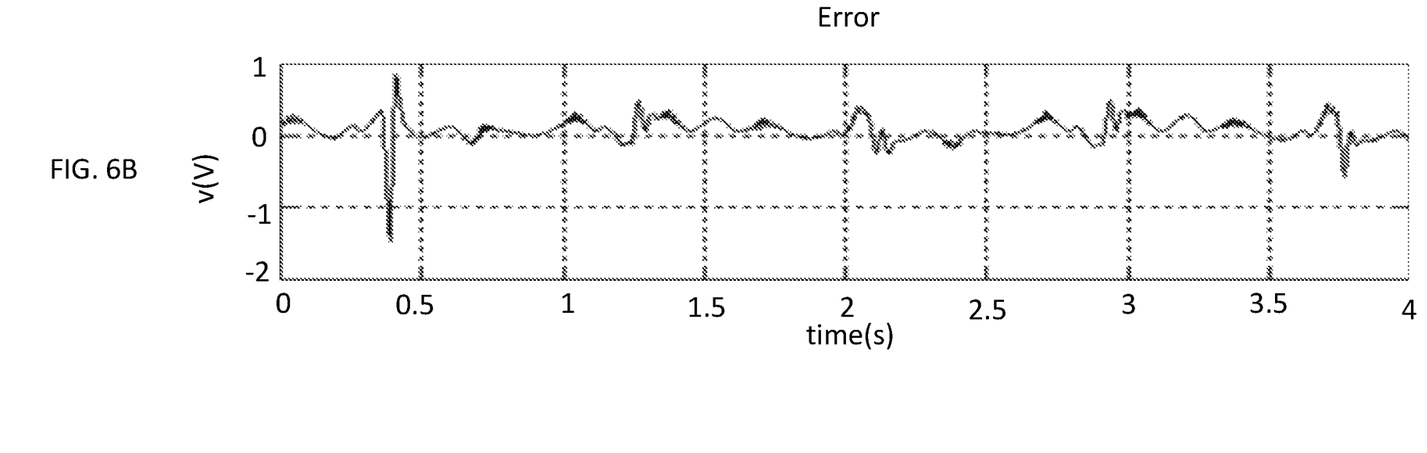
FIG. 6B illustrates the error between the reconstructed output and the bio signal which is scaled according to the gain of the channel.

FIG. 6A illustrate outputs of the two channels of a single biosensor, and FIG. 6B illustrates the error between the reconstructed output and the bio signal which is scaled according to the gain of the channel. FIG. 6A shows signals $V_{out1}$ and $V_{out2}$ of the two channels, where channel 1 has an input capacitance $C_{p1}$=5 pF and channel 2 has $C_{p2}$=50 pF. The motion-induced $C_{in}$ variation distorts the bio signal. The gain is derived with the mean $C_{in}$ value. The root-mean-square deviation is 174 mV and 182 mV for channels 1 and 2, respectively. Thus, the errors of the two outputs are very close.

Figure 7A:
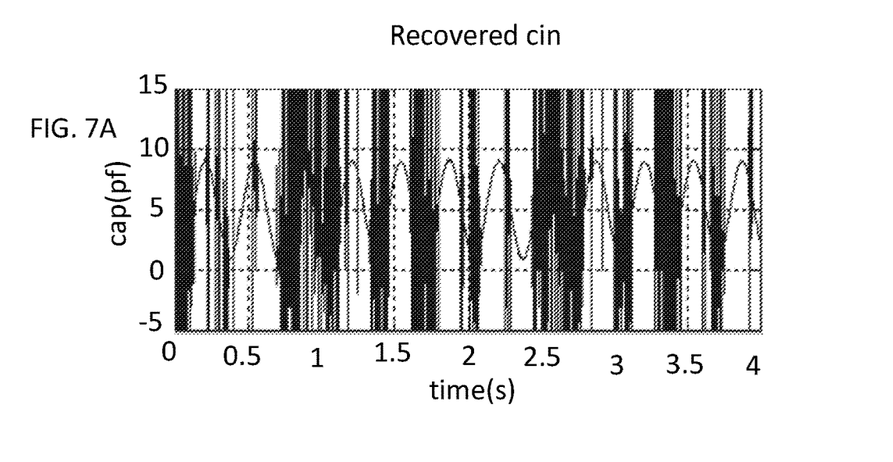
FIGS. 7A-7C respectively illustrate recovered $C_{in}$, the reconstructed signal without filter, and the error.
Figure 7B:
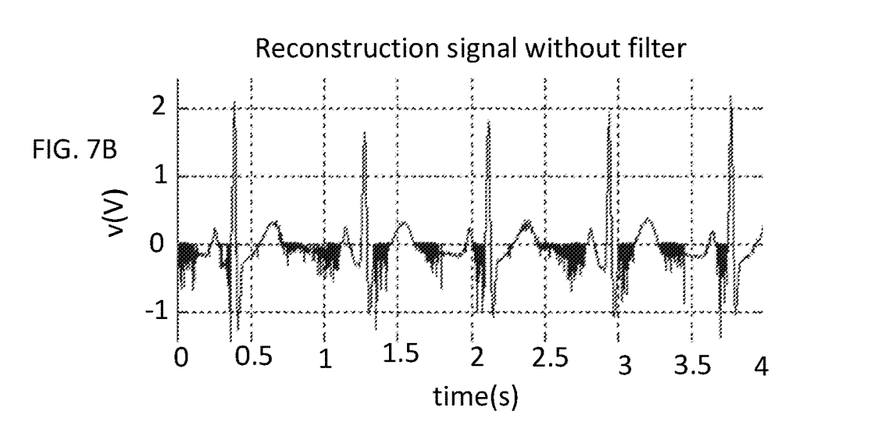
Figure 7C:
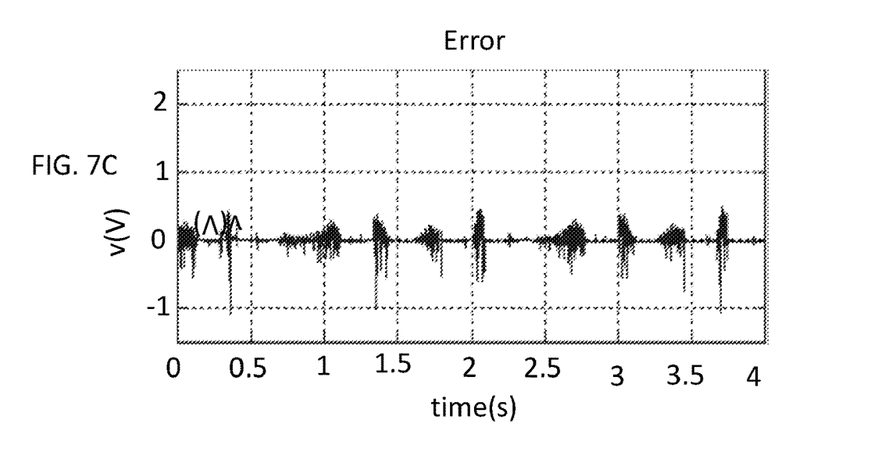

FIGS. 7A-7C respectively illustrate the recovered $C_{in}$, the reconstructed signal without filter, and the error. The data validates equations 6 and 7. Glitches in the FIG. 7A are caused by the finite resolution of the simulation and divide-by-zero errors. The glitches can be easily filtered out in the digital domain. FIG. 7B illustrates the ECG signal after reconstruction (Eq. 7). FIG. 7C illustrates error between the ideal ECG signal and the reconstructed signal. The root-mean-square deviation is 90.1 mV.

Figure 8A:
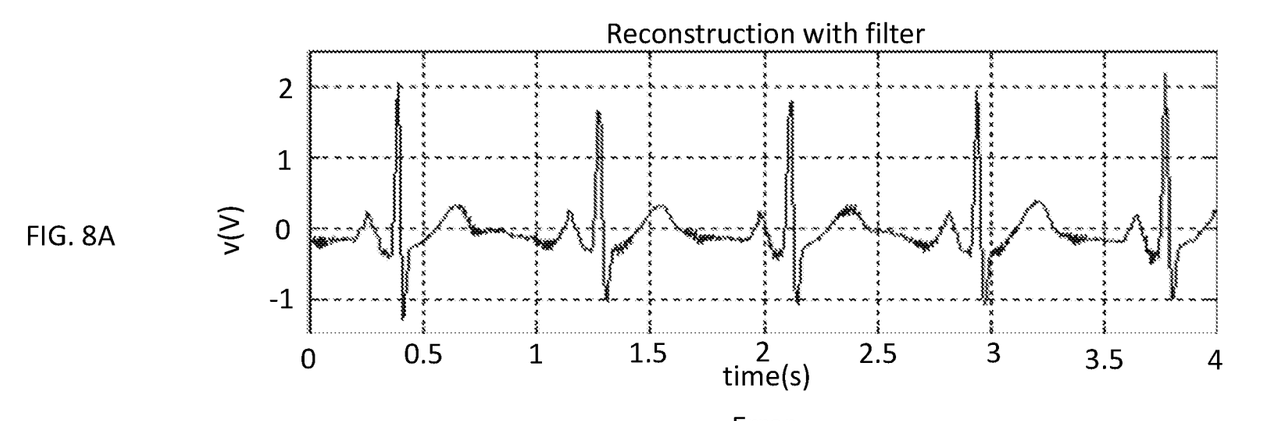
FIGS. 8A and 8B respectively show the post-amplification recovered simulated bio signal and error after a low pass filter with a 100 Hz cut-off frequency.
Figure 8B:
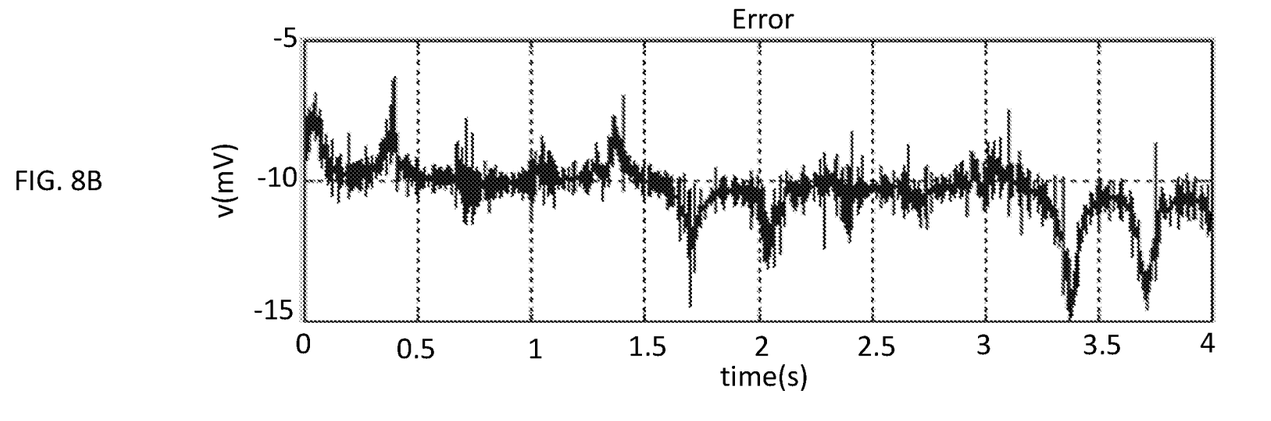

FIGS. 8A and 8B respectively show the post-amplification recovered simulated bio signal and error after a low pass filter with a 100 Hz cut-off frequency. The root-mean-square error is reduced to 12.2 mV (8 µV when referred to the input). Compared to the original errors of 174-182 mV (116-121 µV input-referred), the motion artifact suppression in the preferred embodiment has improved the performance by more than 14×.

While specific embodiments of the present invention have been shown and described above and in the attachments the follow the example claims, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended example claims.

The invention claimed is:

1. A bio sensor, comprising:
   a plurality of same-shaped first electrode sections arranged symmetrically with respect to each other in a first layer, a plurality of same-shaped second electrode sections arranged symmetrically with respect to each other in the first layer interleaved between the first electrode sections and isolated from the first electrode sections, a plurality of same-shaped first shield sections arranged symmetrically with respect to each other in a second layer and arranged opposite corresponding ones of the first electrode sections, a plurality of same-shaped second shield sections arranged symmetrically with respect to each other in the second layer interleaved between the first shield sections and isolated from the first shield sections and arranged opposite corresponding ones of the second electrode sections, wherein the first electrode sections are connected to corresponding ones of the first shield sections and the second electrode sections are connected to corresponding ones of the second shield sections to define at least two shielded electrode channels;
   dielectric isolating electrode sections and shield sections of the at least two shielded electrode channels from each other;
   at least two capacitor plates electrically connected to the at least two shielded electrode channels; and
   packaging to protect the biosensor and permit the biosensor to be worn in a manner to place the at least two capacitor plates adjacent skin of a user.

2. The bio sensor of claim 1, further comprising a signal layer within the packaging including a two channel signal amplifier, wherein the at least two shielded electrode channels provide input capacitances for the two channel signal amplifier.

3. The bio sensor of claim 2, wherein each of the plurality of same-shaped first and second electrode sections and each of the plurality of same-shaped first and second shield sections comprises a pie piece shaped section that is generally triangular with an apex opposite an arcuate end.

4. The bio sensor of claim 3, further comprising vias connecting the plurality of same-shaped first electrode sections to the corresponding plurality of same-shaped first shield sections.

5. The bio sensor of claim 4, further comprising an outer conductive ring connecting the plurality of same-shaped second electrode sections to the corresponding plurality of same-shaped second shield sections.

6. A bio sensor system including a biosensor of claim 1, and further comprising:
   a module including a common noise reduction circuit and a communication module to communicate sensed biosignals to a portable computing device or computer.

7. The system of claim 6, wherein the common noise reduction circuit is configured to:
   obtain biosignals from the at least two capacitor plates through the plurality of same-shaped first and second electrode sections, wherein the at least two shielded electrode channels have different input load capacitances;
   calculate input coupling capacitance for the bio-sensor using the different input load capacitances;
   with the input coupling capacitance and a signal from one of the at least two shielded electrode channels, recover a biosignal of interest.

8. The system of claim 7, wherein the input coupling capacitance is determined as follows:
   output of the at least two shielded electrode channels are calculated $$V_1 = \text{Gain} \times \frac{V_s(t) \times C_{in}(t) + Q_1}{C_{in}(t) + C_{p1}} \ \&$$

$$V_2 = \text{Gain} \times \frac{V_s(t) \times C_{in}(t) + Q_2}{C_{in}(t) + C_{p2}},  \quad\quad 5$$

wherein $C_{p1}$ and $C_{p2}$ are the different input load capacitances, Q(t) is set as a constant representing charge at an amplifier input node, and then the input capacitance is determined by $$C_{in}(t) = \frac{(Q_2 - Q_1) + (C_{p1} \times V_1 - C_{p2} \times V_2)}{V_2 - V_1}.$$

* * * * *